United States Patent [19]
Bowman et al.

[11] Patent Number: 5,730,601
[45] Date of Patent: Mar. 24, 1998

[54] METHOD AND MATERIAL FOR USE WITH DENTAL COMPOSITES FOR IMPROVING CONVERSION OF MONOMERS TO POLYMERS AND REDUCING VOLUME SHRINKAGE

[75] Inventors: Christopher N. Bowman, Nederland, Colo.; Kristi S. Anseth, Boston, Mass.; Anandkumar R. Kannurpatti, Boulder; Michael D. Goodner, Lafayette, both of Colo.

[73] Assignee: The Regents of the University of Colorado, Boulder, Colo.

[21] Appl. No.: 613,348

[22] Filed: Mar. 11, 1996

[51] Int. Cl.⁶ .................................................. A61C 5/00
[52] U.S. Cl. .................. 433/228.1; 433/226; 523/116; 523/118
[58] Field of Search ........................ 433/226, 228.1, 433/215; 523/116, 118

[56] References Cited

U.S. PATENT DOCUMENTS 5,207,577  5/1993  Muller et al. ................ 433/228.1 X
5,276,068  1/1994  Waknine ...................... 433/228.1 X
5,401,783  3/1995  Bowman ...................... 433/228.1 X
5,472,991  12/1995 Schmitt et al. ................ 433/228.1 X
5,534,562  7/1996  Jensen et al. .................. 433/228.1 X

OTHER PUBLICATIONS

Anseth, et al, Polymeric Dental Composites: Properties and Reaction Behavior of Multimethacrylate Dental Restorations, Anseth et al, *Advances In Polymer Science* pp. 179–212, 1995.

*Primary Examiner*—Nicholas D. Lucchesi
*Attorney, Agent, or Firm*—Emery L. Tracy

[57] ABSTRACT

A composition for use in dental treatments of damaged or diseased teeth is provided. The composition comprises a combined filler material, photoinitiator and comonomer resin mixture polymerizable upon incidence of light. The comonomer resin mixture comprises a comonomer resin blend comprising at least two monomers from the same monomer series with at least a first monomer having a first molecular weight and a second monomer having a second molecular weight with the second molecular weight being greater than the first molecular weight of the first monomer. The comonomer resin mixture further comprises a third monomer combined with the comonomer resin blend.

20 Claims, 2 Drawing Sheets

METHOD AND MATERIAL FOR USE WITH DENTAL COMPOSITES FOR IMPROVING CONVERSION OF MONOMERS TO POLYMERS AND REDUCING VOLUME SHRINKAGE

BACKGROUND OF THE INVENTION

1. Field of the Invention

The present invention relates to a method and material for use with dental composites for treating and restoring teeth and, in particular, relates to a method and material for use with dental composites for treating and restoring teeth which improve conversion of monomers to polymers and reduce composite volume shrinkage.

2. Description of the Prior Art

Due to increased public health concerns over using dental amalgams and alloys in treating and restoring teeth, photo-curable dental resins are becoming increasingly popular for dental restorations and fillings. Typically, the dental resins used today are comprised of a mixture of chemicals (known as resin monomers). These resin monomers are, in a molecular sense, small molecules having several C=C double bonds.

In use, the dental resins are mechanically flowed into or about a patient's damaged or diseased tooth and then cured hard by the application of light. The light converts initiator molecules into free radicals which initiate a chain reaction through the monomer double bonds. This "curing" process results in a highly cross-linked, three-dimensional polymer network or matrix having a high mechanical strength, high resistance to temperature and low water sorption characteristics.

While a better alternative to dental amalgams, the high degree of cross-linking that gives dental resins their strength also acts like as "finely meshed 3-D sieve" which limits the mobility of the initiating molecules during the curing process. In fact, during the polymerization of multifunctional monomers for dental restorations, typical final double bond conversions range anywhere from 55–75%. Thus, despite the presence of initiator molecules and unreacted double bonds in the system, the high degree of cross-linking limits any additional conversion. Based on 75% conversion of double bonds, a minimum of 6.25% (25% * 25%) of a divinyl monomer is left without either double bond reacted.

The fact that only 55–75% of the double bonds have reacted directly results, as described above, in some unreacted monomers being present in the final polymer resin composite which is to be used as a dental restoration or filling. It has been shown that unreacted monomer in a dental restoration is a potential health hazard. Residual monomer leaches from the hardened dental polymer composite and into the patient's body where the unreacted monomer may cause sensitization and allergic reactions.

Furthermore, due to unreacted monomers acting as plasticizers, failures in dental composites are directly linkable to problems associated with a dental restoration's durability and wear when the resins are in the highly cross-linked cured state. While the mechanism for the degradation is not completely understood, several factors have been identified as contributing to wear, including induced messes within the dental restoration or filling. The induced stresses occur due to differences in thermal expansion between the actual dental restoration and the tooth structure and volume shrinkage during the polymerization. Thus, due to volume shrinkage, even though the dental cavity was completely filled when the resin composite was injected, the resulting dental restoration and filling recedes slightly from the cavity walls leading to a shortened useful life for the dental restoration or filling.

Others have attempted to improve the conversion of monomers to polymers and to reduce the mechanical shrinking of the composite by increasing the temperature of the resin in the patient's mouth. Unfortunately, conversion improvement and reduction in shrinkage only occurred when the temperature was increased to an unbearable human level which could possibly injure and cause pain to the patient. Therefore, in a practical dental environment, raising the temperature to achieve an increased conversion and decreased shrinkage is not a feasible solution to a serious problem.

SUMMARY

The present invention is a composition for use in dental treatments of damaged or diseased teeth. The composition comprises a filler material, a photoinitiator, and a comonomer resin mixture polymerizable upon incidence of light with the mixture being combined with the filler material.

The comonomer resin mixture of the present invention preferably comprises a comonomer resin blend having at least two monomers from the same monomer series. The comonomer resin blend includes a first monomer having a first molecular weight and a second monomer having a second molecular weight. The second molecular weight is greater than the first molecular weight of the first monomer.

In a preferred embodiment, the viscous monomer comprises approximately between 50–80 wt % of the comonomer resin mixture and the resin comonomer blend comprises approximately between 20–50 wt % of the comonomer resin mixture. Furthermore, the viscous monomer preferably comprises a monomer selected from the group consisting of BIS-GMA, $CH_3$ BIS-GMA and 3F BIS-GMA.

In another preferred embodiment, the second monomer comprises at least 1 wt % of the comonomer resin blend. Preferably, the first monomer comprises approximately between 70–95 wt % of the comonomer resin blend and the second monomer comprises approximately between 5–30% of the comonomer resin blend. Additionally, the first monomer and the second monomer comprise monomers selected from the series consisting of poly(ethylene glycol) dimethacrylates, poly(alkane diol) dimethacrylates, and poly (ethylene diol) dimethacrylates.

In yet another preferred embodiment, the first monomer and the second monomer comprise a poly(ethylene glycol) dimethacrylate and, in particular, the first monomer comprises a monomer selected from the group consisting of diethylene glycol dimethacrylate and triethylene glycol dimethacrylate and the second monomer comprises poly (ethylene glycol 600) dimethacrylate having a molecular weight of approximately between 600–800 g/mol.

In yet another preferred embodiment, the first monomer has a molecular weight less than approximately 286 g/mol and the second monomer has a molecular weight of greater than approximately 286 g/mol. Furthermore, in another preferred embodiment, the average molecular weight of the first and second monomers is greater than approximately 286 g/mol.

The present invention further includes a method for treating damaged or diseased teeth. The method comprises combining at least two monomers from the same monomer series creating a comonomer resin blend. The comonomer resin blend comprises a first monomer resin having a first molecular weight with a second monomer resin having a second molecular weight with the second molecular weight being greater than the first molecular weight of the first monomer resin. Next, a third monomer is mixed with the first and second monomers of the comonomer resin blend to create a comonomer resin mixture and adds strength to the final composite. The third monomer increases the viscosity of the comonomer resin mixture. Then, a photoinitiator is added to the comonomer resin mixture. Next, a filler material is blended into the comonomer resin mixture. Finally, the comonomer resin mixture, photoinitiator and filler material are photopolymerized to convert at least a portion of the first, second and third monomers in the comonomer resin mixture into a copolymer resin composition.

In a preferred embodiment, the third monomer comprises approximately between 50–80 wt % of the comonomer resin mixture and the comonomer resin blend comprises approximately between 20–50 wt % of the comonomer resin mixture. Furthermore, preferably, the third monomer comprises a monomer selected from the group consisting of BIS-GMA, $CH_3$ BIS-GMA and 3F BIS-GMA.

In another embodiment, the second monomer comprises at least 1 wt % of the comonomer resin blend. Preferably, the first monomer comprises approximately between 70–95 wt % of the comonomer resin blend and the second monomer comprises approximately between 5–30% of the comonomer resin blend. Additionally, the first monomer and the second monomer comprise monomers selected from the same series of monomers. The monomer series within the scope of the present invention include, but are not limited to, poly(ethylene glycol) dimethacrylates, poly(alkane diol) dimethacrylates, and poly(ethylene diol) dimethacrylates. An example of a dental resin constructed according to the present invention with the first and second monomer resins being selected from the same monomer series is as follows:

The first monomer resin and second monomer resin comprising a monomer selected from the series poly (ethylene glycol) dimethacrylates. The first monomer resin consists of either diethylene glycol dimethacrylate or triethylene glycol dimethacrylate. The second monomer resin comprising poly(ethylene glycol 600) dimethacrylate.

In an embodiment of the present invention, the first monomer has a molecular weight less than 286 g/mol., the second monomer has a molecular weight of greater than 286 g/mol. and the comonomer resin blend comprises an average molecular weight greater than 286 g/mol.

BRIEF DESCRIPTION OF THE DRAWINGS

The FIGS. 1–6 in the present application are graphs derived from the experimentations by the inventors of the present invention during the invention and reduction to practice of the present invention. The monomers and comonomers illustrated are representative of the types of monomers available for use. Other monomers and comonomers, including the monomers set forth below, are within the scope of the present invention.

DESCRIPTION OF THE PREFERRED EMBODIMENTS

Figure 1:
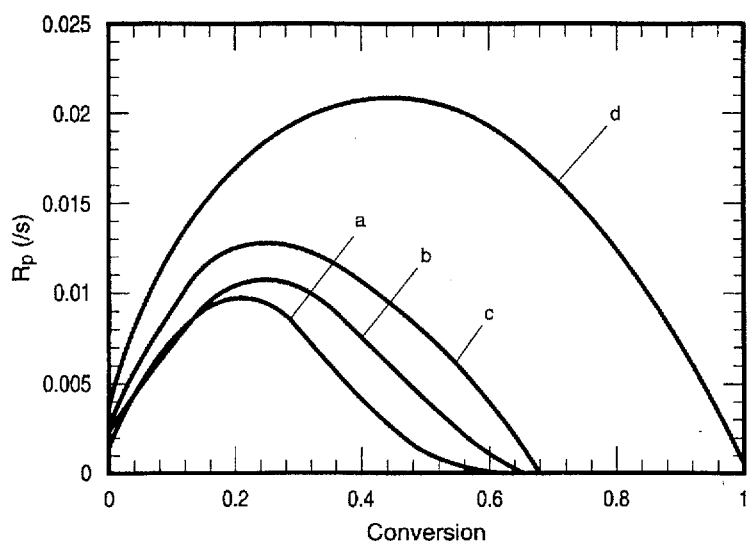
FIG. 1 illustrates the rate of polymerization vs. double bond conversion for homopolymerizations of (a) DEGDMA, (b) TrEGDMA, (c) PEG200DMA, and (d) PEG600DMA.

The manuscript entitled "The Influence of Comonomer Composition on Dimethacrylate Resin Properties for Dental Composites" by Anseth et al. which was presented at the AADR 1995 Annual Meeting, Dallas, Tex., is hereby herein incorporated by reference.

The present invention is a dental restoration composition for use in restoration and filling of teeth. The present invention discloses a systematic approach to formulating a dental restoration composition that reduces the shrinkage in polymer dental fillings and increases the conversion of monomers to polymers. The dental restoration composition of the present invention comprises a filler material, a photoinitiator, and a comonomer resin mixture. The comonomer resin mixture comprises a viscous first monomer resin, and a second comonomer resin blend comprising at least two monomers selected from the same monomer series.

The filler material of the dental composition of the present invention is generally approximately between 45–85 vol %, preferably approximately between 70–80 vol %, of the total dental composition volume. Additionally, the filler material preferably comprises small particles of glass and ceramic. It is, however, within the scope of the present invention to use a filler material comprising strontium aluminofluorosilicate glass or other filler materials could be utilized like inorganic filler materials such as quartz, zinc oxide and barium sulfate, or organic filler materials such as polymethacrylate powder and TEFLON brand powder.

The filler material must, of course, be non-toxic and insoluble in saliva, and of a nature such that the filler material imparts a workable viscosity to the composition enabling molding and manipulation during application. Suitable filler materials are typically inorganic oxides of refractory materials which are clear or white in color. Representative filler materials include polymethylmethacrylate, polyethylmethacrylate, quartz powders, silica gel, colloidal silica, glass beads, alumina oxide, titania oxide, zirconia, silicate glass, aluminosilicate glass and phosphate glass. It is also within the scope of the present invention that the filler material contain leachable fluoride preventing decalcification of the tooth area to which the filler material is adhered.

It is preferred that the filler material be in the form of relatively small particles having an average size of less than one micron. Smaller particle size equates to better adhesion and also, in the case of the filler material containing leachable fluoride, the higher rate of fluoride-release due to the greater surface area of the smaller particles.

The photoinitiator of the dental composition of the present invention effectively catalyzes polymerization of monomers upon irradiation. The photoinitiator acts as a source of free radicals when the dental composition is irradiated with visible light. The photoinitiator of the present invention comprises 2,2-dimethoxy-2-phenylacetophenone. While a certain photoinitiator has been described herein, it is within the scope of the present invention to utilize other photoinitiators or photoinitiating systems achieving the same result. The use of the photoinitiator as a source of free radicals will be described further below.

The comonomer resin mixture is added to the filler material and photoinitiator. The comonomer resin mixture acts as a bonding agent promoting polymeric matrix and filler material cohesion. The comonomer resin mixture of the present invention preferably comprises substantially the remaining 20–30 vol % of the dental composition. In the dental composition of the present invention, as mentioned above, the comonomer resin mixture comprises the viscous monomer resin and a comonomer resin blend comprising at least two monomers, a first monomer resin and a second monomer resin, both selected from the same monomer series. Furthermore, the first monomer resin has a low molecular weight relative to the second comonomer resin having a high molecular weight.

The viscous monomer resin comprises approximately between 65–75 wt % of the comonomer mixture while the comonomer resin blend comprises approximately between 25–35 wt % of the comonomer resin mixture. The exact wt % distribution between the viscous monomer resin and the comonomer resin blend in the comonomer resin mixture is dependent upon a number of factors including flexibility and workability of the dental composition, desired strength of the final dental composition, desired total shrinkage, and desired conversion rate of the monomers to polymers.

The viscous monomer resin preferably consists of a bisphenol-based dimethacrylate or similar substance and is utilized as a stiffening agent in the dental composition. In the present application, the bisphenol-based dimethacrylate includes 2,2 bis[4-(2-hydroxy-3-methacryloyloxyprop-1-oxy) phenyl] propane (BIS-GMA), however, any bisphenol-based dimethacrylate is within the scope of the present invention including, but not limited to, 2,2 bis[4-(2-methacryloxyprop-1-oxy) phenyl] propane ($CH_3$BIS-GMA) and 1,1,1-trifluoro-2,2-bis[4-(2-methacryloxyprop-1-oxy) phenyl]-2-phenyl ethane (3F BIS-GMA). The viscous monomer resin provides a stiffness to the dental composition such that a dentist or other person is able to mold and manipulate the composition. Also, the viscous monomer resin has a molecular structure which imparts strength to the dental composition of the present invention.

As the light converts initiator molecules in the photoinitiator into free radicals, the free radicals initiate a chain reaction through the C=C bonds in the monomer. The result is a highly crosslinked polymer that is typically strong and durable for dental applications. However, due to the short chain, the crosslinking also effectively prevents some of the unreacted monomers and free radicals from reacting together. Therefore, unreacted monomers remain in the converted polymer resin which can cause health problems.

Increasing the conversion of monomers to polymers, the comonomer resin blend comprises a blend of low (short chain) and high (long chain) molecular weight monomer resins selected from the same series of monomers, preferably from the series of poly(ethylene glycol) dimethacrylate monomers. It is within the scope of the present invention to have the first and second monomers of the comonomer resin blend selected from other series of polymerizable dimethacrylate monomers including poly(alkane diol) dimethacrylates and poly(ethylene diol) dimethacrylates.

Using poly(ethylene glycol) dimethacrylates, the low molecular weight or first monomer resin comprises approximately between 70–95 wt % of the comonomer resin blend and preferably comprises di- or tri-ethylene glycol dimethacrylate (DEGDMA or TrEGDMA) having a molecular weight of approximately 242 g/mol and 286 g/mol, respectively. The high molecular weight or second monomer resin comprises approximately between 5–30 wt % of the comonomer resin blend and preferably comprises poly (ethylene glycol 600) dimethacrylate (PEG600DMA) having a molecular weight of approximately between 600–800 g/mol. It is preferred that the average molecular weight of the comonomer resin blend is greater than approximately 286 g/mol.

To achieve beneficial results utilizing at least two monomers from the same monomer series, as little as 1 wt % or less high molecular weight or second monomer needs to be added to the low molecular weight or first monomer. Preferably, maximizing conversion, minimizing polymerization shrinkage, and maintaining mechanical strength, the comonomer resin blend includes the second monomer comprising approximately 30 wt % poly(ethylene glycol) 600 dimethacrylate (longer monomer) and the first monomer comprising 70 wt % diethylene glycol dimethacrylate (shorter monomer). The second monomer resin sweeps through a larger volume of the comonomer resin blend thereby increasing the mobility in the reacting system. The higher mobility enhances the probability that monomers and free radicals will "find each other" thereby resulting in higher conversion of monomers to polymers.

The present invention provides combining high molecular weight monomers with low molecular weight monomers tom the same series of monomers to increase conversion and decrease the shrinkage without compromising the mechanical strength of the dental composition. This technique essentially involves adding a generally small amounts of the high molecular weight monomer. By changing the size and weight percentage of the monomers in the comonomer resin blend, the maximum conversion of monomers to polymers increases while the shrinkage decreases. The addition of the high molecular weight or second monomer maintains suitable mechanical strength and dimensional stability for use as a dental composition.

Having generally described the invention, a more complete understanding can be obtained with reference to a certain specific Example, which is included for purposes of illustration only. It should be understood that the invention is not limited to the specific details of the Example.

EXAMPLE

Materials and Methods

The multifunctional monomers used in the present example were selected from the series consisting of poly (ethylene glycol) dimethacrylate monomers. The commercially available monomers included diethylene glycol dimethacrylate (DEGDMA), triethylene glycol dimethacrylate (TrEGDMA), poly(ethylene glycol 200) dimethacrylate (PEG200DMA), and poly(ethylene glycol 600) dimethacrylate (PEG600DMA) (Polysciences, Inc., Warrington, Pa.) and were used as received from the manufacturer. Bisphenol based dimethacrylate such as 2,2 bis[4-(2-hydroxy-3- methacryloyloxypropoxy) phenyl] propane similar to as described above was used in conjunction with the above listed monomers.

In each of the monomer compositions, a photoinitiator was added. The photoinitiator amount was approximately 0.1 wt % of the total composition and comprised 2,2-dimethozy-2-phenylacetophenone (DMPA, Ciba Geigy, Hawthorn, N.Y.). The monomers and photoinitiator mixture in the Example were photopolymerized with 2 mW/cm$^2$ of 365 nm ultraviolet light. In each experiment, the cure profiles were monitored with a differential scanning calorimeter, (Model DSC-DPA 7, Perkin Elmer, Norfolk, Conn.) adapted with a photocalorimetric accessory capable of producing either monochromatic or full beam ultraviolet light. The differential scanning calorimeter monitors heat flux as a function of reaction time. The heat flux is related to the rate of polymerization of the comonomer mixture.

The light intensity in the experiments was controlled by neutral density filters (Melles Griot, Ivine, Calif.) and the differential scanning calorimeter was cooled with a refrigerated recirculating chiller (CFT-25, NESLAB, Newington, N.H.) enabling isothermal reaction studies near room temperature. Small sample sizes and low initiator concentrations were chosen insuring the applicability of the thin film approximation for uniform light intensity across the sample. In addition, the differential scanning calorimeter cell was flushed with nitrogen approximately ten minutes prior to the polymerization and continuously during the polymerization since oxygen is a well-known inhibitor of these reactions. Using the heat of reaction per double bond (13.1 kcal/mol for a methacrylate double bond), the conversion as a function of time was determined.

The mechanical properties of the cured dental composition were measured using a dynamic mechanical analyzer (DMA 7, Perkin Elmer, Norwalk, Conn.) in the extension mode. Samples were prepared by photopolymerizing the desired monomer resin in a mold having dimensions 1 mm×3 mm×20 mm. Polymerization conditions matched those of the differential scanning calorimeter studies (2 mW/cm$^2$ of 365 nm ultraviolet light and 0.1 wt % photoinitiator). The modulus of the cured polymer film was monitored as a function of temperature at a frequency of 1 Hz.

Results and Discussion

In the testing, the polymerization rate was normalized by the initial concentration of double bonds in each monomer, ranging from approximately 8.7 mol/L in DEGDMA to approximately 2.9 mol/L in PEG600DMA. As illustrated in FIG. 1, the reaction profiles are shown for the homopolymerization of the dimethacrylate monomers. A review of FIG. 1 reveals that distinct regions of autoacceleration and autodeceleration in the polymerization rate result from diffusion control of the termination and propagation reaction, respectively. Since the monomers polymerize to form highly crosslinked polymer networks and the system gels at very low double bond conversions, mobility of the reacting species is severely reduced even at low conversion. Ultimately, the system reaches a maximum attainable double bond conversion. It was determined that the maximum conversion of the monomers is strongly dependent on the molecular weight of the monomer (i.e., the maximum conversion is greatly influenced by the initial concentration of double bonds in the system). The maximum conversions range from 0.58 for DEGDMA to 0.65 for TrEGDMA to 0.68 for PEG200DMA to 1.00 for PEG600DMA.

For dental restorative materials, it is desirable to develop resins that approach 100% conversion of double bonds upon completion of the cure to reduce residual monomer concentrations in the crosslinked polymer resin. From the experiments conducted for the present invention, monomers of higher molecular weight and lower double bond concentrations were used. However, by using only higher molecular weight monomers, the crosslinking density of the final polymer network was reduced. To overcome the reduced density, the inventors of the present application, copolymerized several higher molecular weight monomers with lower molecular weight monomers. The objective was to optimize the double bond conversion in the system without altering the crosslinking density of the final polymer network to the extent that the mechanical properties of the network were diminished.

Figure 2:
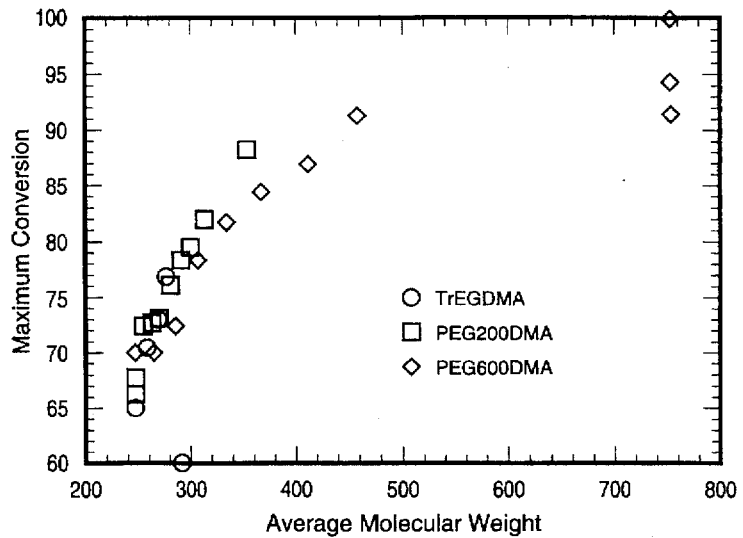
FIG. 2 illustrates the maximum attainable double bond conversion vs. average molecular weight of monomer resin for copolymerizations of (o) DEGDMA with TrEGDMA, (□) DEGDMA with PEG200DMA, and (◊) DEGDMA with PEG600DMA.

FIG. 2 illustrates the maximum attainable double bond conversion as a function of the average molecular weight of the monomer resin for several copolymerizations including DEGDMA with TrEGDMA, DEGDMA with PEG200DMA, and DEGDMA with PEG600DMA. Interestingly, the inventors of the present application discovered that the maximum double bond conversion increases monotonically with the increasing molecular weight of the monomer resin. As discussed above, this increase in the maximum conversion results from a decrease in the initial concentration of double bonds. Since fewer double bonds are initially present (and nearly the same number of double bonds react in each system), the final conversion in the system increases. The increased maximum conversion translates into a lower amount of residual monomer in the final polymer matrix. The increased conversion is desirable to improve biocompatibility and reduce swelling.

From FIG. 2, it is also evident that different higher molecular weight monomers affect the maximum double bond conversion differently. For example, when TrEGDMA or PEG600DMA are copolymerized with DEGDMA, the maximum double bond conversion is enhanced to a similar extent in both systems. In contrast, the addition of PEG200DMA to the polymerization mixture increases the maximum double bond conversion to a greater extent than that of either TrEGDMA or PEG600DMA at similar average molecular weights in the monomer resin. For example, at an average resin molecular weight of 300 g/mol, the maximum double bond conversion in poly(PEG200DMA-co-DEGDMA) is approximately 85%, while poly(TrEGDMA-co-DEGDMA) and poly(PEG600DMA-co-DEGDMA) are approximately 80%.

Next, the testing determined the fraction of unreacted double bonds that are monomeric (i.e., unattached to the network) versus pendant (i.e., attached to the network). In terms of biocompatibility of the polymer matrix, reducing the amount of unreacted monomeric double bonds is critical to limit the risks associated with leaching of these small molecules. Gelation simulations were performed to gain a better understanding and to establish further the importance of increased double bond conversion on the monomeric double bond conversion. Kinetic gelation simulations are percolation-type simulations for studying the free radical copolymerization of mono- and multifunctional monomers in any relative proportions.

The primary advantage of kinetic gelation simulations for highly crosslinked system (homopolymerizations of multifunctional monomers) is the ability to predict heterogeneity. Heterogeneity leads to unequal reactivity of the monomeric and pendant double bonds. In the initial phase of the polymerization, all of the pendant double bonds are close to active centers, i.e., radicals, which makes the pendant double bonds highly reactive. This effect increases the amount of unreacted monomer present at a given conversion.

Figure 3:
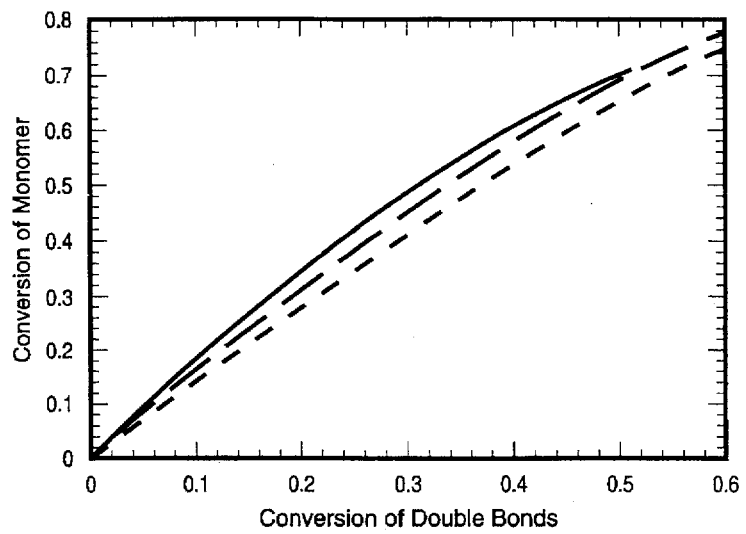
FIG. 3 illustrates kinetic gelation simulation results for the influence of monomer size on the conversion of monomer as a function of the conversion of double bonds (———) 3-site, (———) 5-site, and (—) 10-site monomers.

FIG. 3 illustrates kinetic gelation simulation results for the influence of the monomer size (i.e., molecular weight) on the conversion of monomer as a function of the conversion of double bonds. Specifically, the fraction of monomer which has at least one double bond reacted is plotted as a function of double bond conversion for a three-, five-, and ten-site monomer molecule (representing an increase one might associate with the increase in size from DEGDMA to TrEGDMA to PEG600DMA).

From FIG. 3, two results were discovered. First, as the monomer size is increased (e.g., from three sites to ten sites) at a given conversion, the amount of residual monomer is dramatically decreased. This decrease in residual monomer is the result of a reduced relative reactivity of the pendant double bonds relative to the monomeric double bonds as the size of the monomer molecule is increased. As the monomeric double bonds become more reactive, the fraction of monomer that remains unreacted decreases.

Second, as the double bond conversion increases, the residual monomer fractions decrease markedly. Reviewing the three-site monomer molecule, as the double bond conversion increases from 50 to 60% the amount of monomer that has at least one double bond reacted increases from 63% to 75%. The conversion increase reduces the residual monomer by nearly one third. Thus, it was discovered that by copolymerizing lower and higher molecular weight monomer molecules, the double bond conversion and the monomer conversion are both significantly increased.

In addition to determining the influence of monomer molecular weight on conversion, the volume shrinkage during polymerization was also characterized. During polymerization, a certain amount of volume (22.5 cm³/mol) is consumed for each methacrylate double bond that reacts. Because of this relationship between double bond conversion and polymerization shrinkage, it was determined that minimizing the total number of double bonds that react will minimize volume shrinkage during curing of the monomer resin. Hence, the comonomer resin compositions with higher average molecular weights will also have a lower concentration of double bonds which reduces the potential for shrinkage during polymerization.

Figure 4:
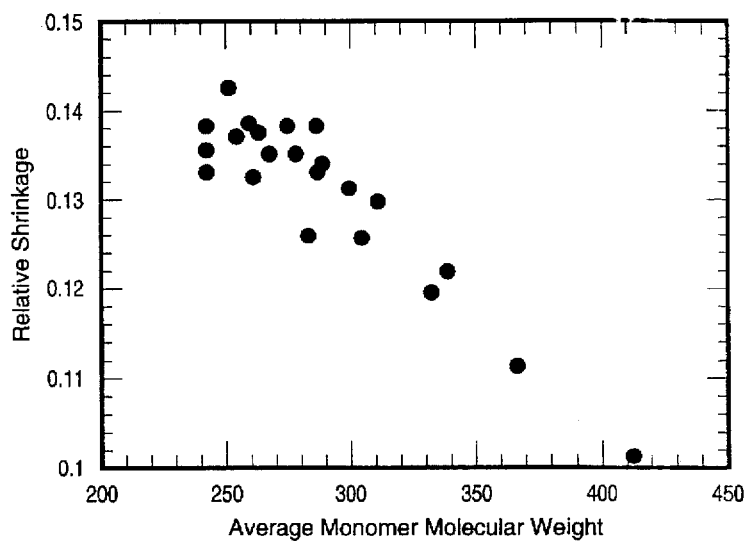
FIG. 4 illustrates predicted relative volume shrinkage upon full cure as a function of average weight of monomer resin for copolymerizations of DEGDMA with TrEGDMA, DEGDMA with PEG200DMA, and DEGDMA with PEG600DMA.

FIG. 4 illustrates the predicted relative volume shrinkage upon completion of the polymerization as a function of the average molecular weight of the monomer resin. The resin compositions studied were DEGDMA copolymerized with varying weight percent of TrEGDMA, PEG200DMA, or PEG600DMA. In general, it was determined that the volume shrinkage decreases with increasing average molecular weight of the monomer resin. While the reduction in polymerization shrinkage will reduce stresses that cause adhesive failure (marginal leakage) and/or cohesive failure (microcracking of the composite), the crosslinking density of the polymer matrix has been changed. Therefore, increasing the molecular weight of the monomer resin not only enhances the double bond conversion and reduces the polymerization shrinkage, but also decreases the crosslinking density of the polymer which is detrimental to the mechanical properties of the network.

Figure 5:
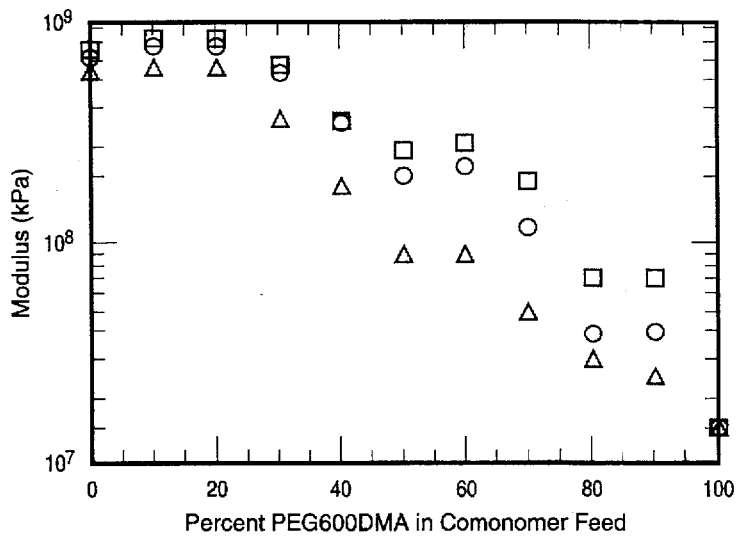
FIG. 5 illustrates tensile modulus vs. weight percent PEG600DMA in poly(DEGDMA-co-PEG600DMA) at (□) 25° C., (o) 40° C. and (△) 80° C.

As illustrated in FIG. 5, the influence of the monomer resin composition and molecular weight on the mechanical properties of the final polymer matrix were examined. FIG. 5 illustrates the tensile modulus as a function of weight percent PEG600DMA in poly(DEGDMA-co-PEG600DMA) at three different temperatures ranging from 25° C. to 80° C. From this figure, several trends are apparent. First, as the temperature is increased, the modulus of the polymer is decreased. This decrease results from the higher thermal energy which increases the chain mobility and decreases the modulus of the polymer. Second, over the entire composition range, the modulus of the network decreases nearly two orders of magnitude from approximately $10^9$ Pa for poly(DEGDMA) to approximately $10^7$ Pa for poly(PEG600DMA). Macroscopic observations show poly(DEGDMA) is a glassy network at room temperature whereas poly(PEG600DMA) is rubbery.

Finally, from examining the modulus between 0 and 30 wt % of PEG600DMA in DEGDMA, FIG. 5 illustrates that adding from 0 to 20 wt % PEG600DMA to the monomer resin does not change the modulus of the final polymer network. Extending the region even further to 30 wt % of PEG600DMA, the modulus changes by less than 10%. The average molecular weight of a monomer resin with 30 wt % PEG600DMA and 70 wt % DEGDMA is 395 g/mol. Therefore, within certain limits, increasing the molecular weight of the monomer resin and decreasing the concentration of double bonds in the system is an effective approach to increasing the conversion and reducing the polymerization shrinkage, while maintaining the mechanical strength of the polymer.

Figure 6:
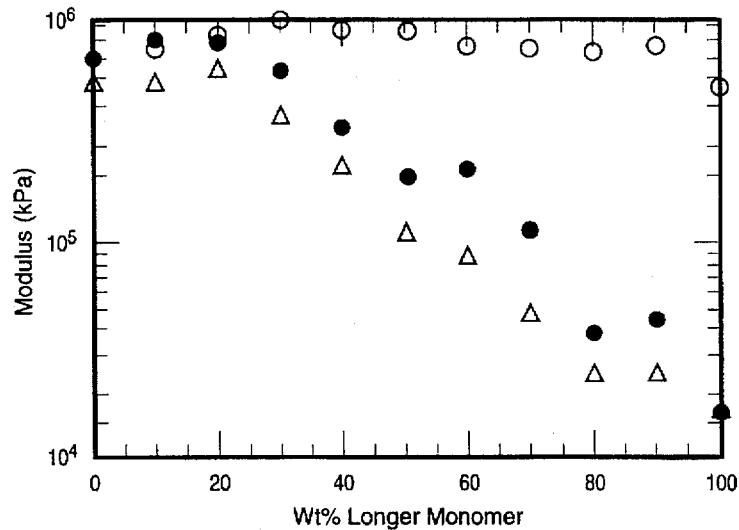
FIG. 6 illustrates modulus at 40° C. vs. weight percent of longer monomer for (△) poly(PEG600DMA-co-DEGDMA), (o) poly(PEG200DMA-co-DEGDMA), and (●) poly(PEG600DMA- co-PEG200DMA).

FIG. 6 illustrates the modulus plotted as a function of weight percent of the highest molecular weight monomer for several monomer resin compositions. The copolymers studied were poly(PEG600-co-DEGDMA), poly (PEG200DMA-co-DEGDMA), and poly (PEG600DMA-co-PEG200DMA), and the modulus was measured at 40° C. Again, the results reinforce that up to 30 wt % of a higher molecular weight monomer can be added to the monomer resin without detrimentally altering the modulus of the final polymer network.

To summarize, the research conducted by the inventors of the present application supports that with the model poly (ethylene glycol) dimethacrylate monomer series, the optimization of copolymer composition can lead to significant increases in the maximum attainable conversion. Additionally, this increase in conversion is accompanied with a slight decrease in polymerization shrinkage and no significant decrease in the mechanical strength.

End of Example

As has been described, the present invention is a dental restoration composition utilizing a comonomer resin blend comprising at least two monomers selected from the same series of monomers and has at least two distinct advantages over known dental compositions. In the present invention, the viscous monomer resin (preferably, BIS-GMA) is combined with a comonomer resin blend having a first monomer resin and a second monomer resin having a longer chain separating the C=C bonds with both the first and second monomer resins being selected from the same monomer series. As discussed, the second monomer resin has a higher molecular weight than the first monomer resin and is crosslinkable to form a polymer, similar to the first monomer. The longer chains sweep through a larger volume thereby increasing the mobility of the free radicals in the reacting system. Therefore, using a combination of the first and second monomer resins of the present invention, fewer unreacted total monomers remain increasing conversion of the monomers and reducing the health hazard from such species.

Furthermore, in the dental composition of the present invention, the final polymer is actually formed by the chemical linking of the monomers. As a general rule, the crosslinked monomers occupy a lesser volume than the unlinked monomers thereby exhibiting shrinkage. The long chain monomers as utilized in the present invention have a lower linear concentration of C=C double bonds, so upon polymerization pack less closely, and thus suffer less volume shrinkage. The result is the dental restoration composition of the present invention exhibiting less shrinkage and remaining more snugly in contact with the wall of the tooth surface surrounding the cavity.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

We claim:

1. A composition for use in dental treatments of damaged or diseased teeth, the composition comprising:

a filler material;

a photoinitiator combined with the filler material; and a comonomer resin mixture polymerizable upon incidence of light, the mixture being combined with the filler material and the photoinitiator, the mixture comprising:

a comonomer resin blend comprising at least a first monomer having a first molecular weight and a second monomer having a second molecular weight, the second molecular weight being greater than the first molecular weight of the first monomer; and a third monomer combined with the comonomer resin blend.

2. The composition of claim 1 wherein the third monomer comprises approximately between 50–80 wt % of the comonomer resin mixture and the comonomer resin blend comprises approximately between 20–50 wt % of the comonomer resin mixture.

3. The composition of claim 1 wherein the third monomer comprises a monomer selected from the group consisting of BIS-GMA, $CH_3$ BIS-GMA and 3F BIS-GMA.

4. The composition of claim 1 wherein the second monomer comprises at least 1 wt % of the comonomer resin blend.

5. The composition of claim 1 wherein the first monomer comprises approximately between 70–95 wt % of the comonomer resin blend and the second monomer comprises approximately between 5–30% of the comonomer resin blend.

6. The composition of claim 5 wherein the first monomer comprises a monomer selected from the group consisting of diethylene glycol dimethacrylate and triethylene glycol dimethacrylate and the second monomer comprises poly (ethylene glycol 600) dimethacrylate.

7. The composition of claim 1 wherein the first monomer and the second monomer comprise monomers selected from the series consisting of poly(ethylene glycol) dimethacrylates, poly(alkane diol) dimethacrylates, and poly (ethylene diol) dimethacrylates.

8. The composition of claim 1 wherein the comonomer resin blend comprises at least two monomers from the same monomer series.

9. The composition of claim 1 wherein the second monomer has a molecular weight of greater than 286 g/mol.

10. The composition of claim 1 wherein the resin blend comprises an molecular weight greater than 286 g/mol.

11. A method for restoring a lesion in a tooth, the method comprising;

combining at least two monomer resins creating a comonomer resin blend, the comonomer resin blend comprising a first monomer resin having a first molecular weight with a second monomer resin having a second molecular weight, the second molecular weight being greater than the first molecular weight of the first monomer resin;

mixing a third monomer with the first and second monomers to create a comonomer resin mixture, the third monomer increasing the viscosity of the comonomer resin mixture;

adding a photoinitiator to the comonomer resin mixture;

blending a filler material into the comonomer resin mixture; and photopolymerizing the comonomer resin mixture, photoinitiator and filler material to convert at least a portion of the first, second and third monomers in the comonomer resin mixture into a copolymer resin composition.

12. The method of claim 11 wherein the third monomer comprises approximately between 50–80 wt % of the comonomer resin mixture and the comonomer resin blend comprises approximately between 20–50 wt % of the comonomer resin mixture.

13. The method of claim 11 wherein the third monomer comprises a monomer selected from the group consisting of BIS-GMA, $CH_3$ BIS-GMA and 3F BIS-GMA.

14. The method of claim 11 wherein the second monomer comprises at least 1 wt % of the comonomer resin blend.

15. The method of claim 11 wherein the first monomer comprises approximately between 70–95 wt % of the comonomer resin blend and the second monomer comprises approximately between 5–30% of the comonomer resin blend.

16. The method of claim 11 wherein the first monomer and the second monomer comprise monomers selected from the series consisting of poly(ethylene glycol) dimethacrylates, poly(alkane diol) dimethacrylates, and poly (ethylene diol) dimethacrylates.

17. The method of claim 16 wherein the first monomer comprises a monomer selected from the group consisting of diethylene glycol dimethacrylate and triethylene glycol dimethacrylate and the second monomer comprises poly (ethylene glycol 600) dimethacrylate.

18. The composition of claim 16 wherein the comonomer resin blend comprises at least two monomers from the same monomer series.

19. The method of claim 11 wherein the second monomer has a molecular weight of greater than approximately 286 g/mol.

20. The method of claim 11 wherein the comonomer resin blend comprises an average molecular weight greater than approximately 286 g/mol.

* * * * *